(12) United States Patent
Rippinger et al.

(10) Patent No.: US 12,239,751 B2
(45) Date of Patent: Mar. 4, 2025

(54) UV PATHOGEN CONTROL DEVICE AND SYSTEM

(71) Applicant: GOLD MINE IDEAS, LLC, Nashville, TN (US)

(72) Inventors: Denise Rippinger, Lake Geneva, WI (US); Denny Beasley, LaGrange Park, IL (US)

(73) Assignee: Gold Mine Ideas, LLC, Nashville, TN (US)

( * ) Notice: Subject to any disclaimer, the term of this patent is extended or adjusted under 35 U.S.C. 154(b) by 888 days.

(21) Appl. No.: 17/298,503

(22) PCT Filed: Nov. 29, 2019

(86) PCT No.: PCT/US2019/063836
§ 371 (c)(1),
(2) Date: May 28, 2021

(87) PCT Pub. No.: WO2020/113149
PCT Pub. Date: Jun. 4, 2020

(65) Prior Publication Data
US 2022/0047736 A1    Feb. 17, 2022

Related U.S. Application Data

(60) Provisional application No. 62/772,194, filed on Nov. 28, 2018.

(51) Int. Cl.
*A61L 2/10* (2006.01)
*A61L 2/20* (2006.01)
*A61L 2/26* (2006.01)

(52) U.S. Cl.
CPC ............. *A61L 2/10* (2013.01); *A61L 2/202* (2013.01); *A61L 2/26* (2013.01); *A61L 2202/11* (2013.01); *A61L 2202/16* (2013.01); *A61L 2202/20* (2013.01)

(58) Field of Classification Search
CPC ........ A61L 2/10; A61L 2/202; A61L 2202/11; A61L 2202/16
See application file for complete search history.

(56) References Cited

U.S. PATENT DOCUMENTS

| | | | | |
|---|---|---|---|---|
| 2003/0086848 A1* | 5/2003 | Saccomanno | ........... | C02F 1/325 422/305 |
| 2003/0170151 A1* | 9/2003 | Hunter | ................... | B01J 19/123 588/303 |
| 2005/0186108 A1* | 8/2005 | Fields | ..................... | A61L 2/202 422/123 |
| 2007/0228289 A1* | 10/2007 | Kaszuba | ................ | B05D 3/067 250/492.1 |
| 2013/0093322 A1* | 4/2013 | Borsuk | ................. | H01J 65/044 315/39.51 |
| 2013/0175460 A1* | 7/2013 | Farren | ....................... | A23L 3/28 250/504 R |

* cited by examiner

*Primary Examiner* — Randy Boyer
(74) *Attorney, Agent, or Firm* — Stites & Harbison, PLLC; Richard S. Myers, Jr.

(57) ABSTRACT

A UV microorganism inhibiting device that includes a housing having an interior, and a front and back that defines a length; at least one UV light source located within the interior of the housing; a pressurized air source to produce pressurized air; an inlet for introducing pressurized air into the interior of the housing; a reflective surface within the interior of the housing; and an outlet opening for allowing UV light and an air and ozone mixture to pass from the interior of the housing to outside the housing.

13 Claims, 8 Drawing Sheets

UV PATHOGEN CONTROL DEVICE AND SYSTEM

RELATED APPLICATIONS

This application claims priority from International Patent Application No. PCT/US2019/063836, filed Nov. 29, 2019, which claims benefit to U.S. Provisional Application Ser. No. 62/772,194 filed Nov. 28, 2018, the entire disclosures of which are incorporated herein by this reference.

FIELD OF THE INVENTION

The present is in the technical field of sterilization of surfaces, including both inorganic and organic surfaces.

BACKGROUND OF THE INVENTION

Aspects of the present invention meet a long felt need in that they have a beneficial use in people populated areas such as work environments, schools, restaurants, airports, senior living facilities including any other environment needing to eradicate germs on skin surfaces as well as inorganic surfaces. People in various settings or environments subjected to germs by hand contact will have peace of mind that their hands have been sterilized by a device that kills the germs instantly and continues to kill the germs for a period of time thereafter.

Current liquid/gel hand sanitizers which are applied directly to the hands of a person often leave residual effects. For example, the unpleasant smell and texture remain on the skin after the liquid/gel is rubbed in. In addition, typical liquids/gel are slow drying and leave the hands sticky and cool and unpleasant to be touched by when used by a medical professional. Even further, unknown to most, the liquid/gels commonly used are often highly flammable. Even more problematic is that repeated use of sanitizing liquids/gels can result in a buildup of tolerance and the reduction of effectiveness of the liquid/gels on the pathogens over time.

The use of UV light to kill pathogens is well known. For example, U.S. Pat. No. 6,264,888 to Palestro discloses a germicidal method and apparatus for destroying airborne pathogenic bacteria such as tuberculosis bacteria using ultraviolet light. Air is drawn through a filter and into a sterilization chamber that is irradiated with ultraviolet light, and out through an exhaust opening. Consideration for the characteristics of the room in which the apparatus is installed and the positioning of the installation allows effective prevention of transmission of disease through expectoration and inhalation of airborne microdroplets of bacteria-containing sputum. The filter is of the low-density type which traps large particulates, but not small particulates of the size of the microdroplets, so that the filter does not become a bacteria colonization site. Baffles on the air intake opening and air exhaust opening to prevent ultraviolet light from escaping into the environment. The sterilization chamber is constructed such that the air passes the ultraviolet light bulbs twice as it circulates therethrough.

Further, U.S. Pat. No. 6,497,840 also to Palestro discloses a germicidal method and apparatus for destroying airborne pathogenic bacteria such as tuberculosis bacteria using ultraviolet light. Air is drawn through a filter and into a sterilization chamber that is irradiated with ultraviolet light, and out through an exhaust opening. Consideration for the characteristics of the room in which the apparatus is installed and the positioning of the installation allows effective prevention of transmission of disease through expectoration and inhalation of airborne microdroplets of bacteria-containing sputum. The filter is of the low-density type which traps large particulates, but not small particulates of the size of the microdroplets, so that the filter does not become a bacteria colonization site. Baffles on the air intake opening and air exhaust opening to prevent ultraviolet light from escaping into the environment.

However, these patents fail to describe a UV pathogen control device and system which is easy to use and efficient. Further, these patents fail to provide for a UV pathogen control device and system which utilizes high velocity UV light from multiple reflective surfaces to kill pathogens.

SUMMARY OF THE INVENTION

One aspect of the present invention is a device that inhibits microorganisms on a surface.

In another aspect of the present invention is a device that inhibits microorganism on a surface through the use of a UV light source and ozone.

In another aspect of the present invention, the device is a UV microorganism inhibiting device that includes a housing having an interior, and a front and back that defines a length. The housing includes at least one UV light source located within the interior of the housing, an inlet for introducing pressurized air into the interior of the housing, a reflective surface within the interior of the housing, and an outlet opening for allowing UV light and air to pass from the interior of the housing to outside the housing.

In another aspect of the invention, the reflective surface within the interior of the housing is at least a portion of the interior facing surface of the housing. The reflective surface can be a coating or painted surface.

In another aspect of the invention, the housing has first and second sides, a top and bottom; wherein the first and second sides are non-parallel, with their lines of axis meeting in front of the front of the device. In another aspect, the housing is generally tear-drop shaped, having a smaller front than the back, with the back being generally curved.

In another aspect of the invention, the UV light source is a mercury lamp, xenon lamp, krypton lamp, metal halide lamp, tungsten halogen lamp, quartz halogen lamp, a quartz iodine lamp, a sodium lamp, an incandescent lamp, and combinations thereof.

In another aspect of the invention, the UV light source inherently produces ozone. In other aspects of the invention, the device further comprises an ozone generation source in the housing interior.

In another aspect of the invention, the device comprises at least one planar reflective plate in the interior of the housing.

In another aspect of the invention the device comprises a plurality of planar reflective plates arranged along the length of the interior of the housing. Channels can be formed between the plates that reflect UV light.

In another aspect of the invention, the reflector plates are arranged non-parallel with one another, with the ends of the plates toward the bottom side of the housing closer together than the ends of the plates toward the top of the housing.

In another aspect of the invention, the device includes at least three plates. In another, the device includes at least four plates.

In another aspect of the invention, the device further includes an air compressor and a control panel to direct pressurized air flow into the device interior and to control operation of the light source.

In another aspect of the invention, the device further includes optical sensors at or near the optical opening to measure UV light and ozone levels.

Another aspect of the invention is a UV microorganism inhibiting device that includes a control panel; a housing defining an interior space and having reflective interior surface, and having a top, bottom, and a first side and second side that defines the housing's length; at least one UV light source located within the interior of the housing; a pressurized air source; an inlet for introducing pressurized air into the interior of the housing; a plurality of planar reflective plates arranged along the length of the interior; and an outlet opening for allowing UV light and air to pass from the interior of the housing to outside the housing.

More particularly, an aspect of the present invention is a device that sterilizes through combination wave lengths in the UV spectrum and certain chemical effects caused by UV when in the presence of certain gases.

More particularly, the present invention is in the technical field of sterilization in environments such as medical facilities and the prevention of pathogenic proliferation by people and objects. In the present are toxic chemicals with lasting environmental impact in the form of waste. This waste is created by remaining empty plastic containers once their sterilization action is complete.

An aspect of the present invention is a UV pathogen control device and system which utilizes high velocity air flow in conjunction with UV light from multiple reflective surfaces to kill pathogens.

Another aspect of the present invention is a method of controlling microorganisms on a surface, comprising activating a UV device of the present invention such that airflow from the device is directed to the surface to be treated.

Another aspect of the present invention is a device and method combining high velocity air flow, UV light energy, and ozone production to achieve antisepsis when exposed to the device.

In another aspect of the invention, the surface is skin, including human skin, and other organic objects. In other aspects, the surface is clothing. In another aspect, the surface is an interior space such as a room in a structure. In another aspect of the invention, the surface is an inorganic object. In another aspect, the surface is an area that is contacted by humans or other mammals. In another aspect of the present invention, the surface is living. In another aspect of the invention, the surface is non-living.

In another aspect of the invention, the device is handheld.

Another aspect of the invention is a handheld sanitizing apparatus, as for pathogen reduction on a surface, that includes a housing defining an interior space, with an outlet opening communicating with the interior, and a portion of the housing adapted to be gripped by a user; a ultraviolet (uv) light source mounted within the housing interior, the uv source being chosen to provide one or more wavelengths of light suitable for killing selected pathogens, the uv source mounted in a manner for light to exit through the outlet; a source of gaseous medium which communicates with the housing interior and exits through the outlet in a stream to contact a surface to be treated by the apparatus; the housing interior having one or more reflective surfaces arranged to reflect uv light toward the outlet; at least part of the gaseous medium including oxygen, the uv light generating ozone within the apparatus interior which is expelled with the stream, the amount of ozone generated and expelled being sufficient to kill selected pathogens exposed to the stream.

In one aspect, the gaseous medium is ambient air. In one aspect, the source of gaseous medium is a compressed air source.

In one aspect, the uv light source comprises plural different wavelengths.

In one aspect, the reflecting surface includes a plurality of elongated reflectors forming channels extending from the uv light source a on end to the outlet. In one aspect, the channels are wider in diameter at the uv light source and decreasing in diameter toward the outlet. In another, an angle of incidence of the uv light on sidewalls of the channels is shallow to promote reflectance toward the outlet.

Another aspect of the present invention is a means of sterilization, applicable to all surfaces, but primarily intended for rapid sterilization of skin surfaces while leaving said surface without chemical noticeable substance residuals. This method requires no additional active chemicals and none that are carcinogenic. When used on the hands dexterity and accurate grasp is preserved. No chilling effects from evaporation of water or other volatile compounds. The absence of the slime effect will enhance use and reduce the psychological reticence that current cold slimy compounds have that are typically used by medical practitioners today.

The lack of residual chemical waste reduces and eliminates the expense of disposal as well as contributing to landfills. It eliminates the need for restocking and storage of these compounds. The sterilizing effects are available instantly. No ordering, stocking, storage and waste as we know it to be today.

The UV pathogen control device and system is especially suitable for organic and inorganic sterilization of surfaces through the combination of introduction of wave lengths in the UV spectrum and the chemical effects caused by UV in the presence of certain gases. The device is suitable for use in, for example, medical facilities, schools, restaurants, airports, senior living centers and the typical office space to prevent the proliferation of pathogens by people and objects. The present device also reduces the buildup of environmental waste from plastic bottles caused by current use of disposable sterilization devices like gels and liquids in plastic bottles.

An advantage of the present UV pathogen control device and system is that the present device and system concentrates and focuses air flow in conjunction with UV light toward a pathogen.

Another advantage of the present UV pathogen control device and system is that the present device and system uses multiple reflective surfaces to focus multiple UV light beams toward a surface to be sterilized.

Yet another advantage of the present UV pathogen control device and system is that the present device and system continues to kill pathogens even after the UV light is no longer turned on. With respect to skin, for example, the antiseptic effect persists after ozone dissipation within the skin layers, and degrades into a weaker oxidizing agent, $H_2O_2$.

An advantage of the present UV pathogen control device and system is that the present device and system will not result in pathogen resistance.

An advantage of the present UV pathogen control device and system is that the present device and system uses only minimal energy input to operate.

Yet another advantage of the present UV pathogen control device and system is that the present device and system reduces the inventory stocking requirement and saves space which is typically required for storing liquid/gel bottles.

And an advantage of the present UV pathogen control device and system is that the present device and system allows a user to immediately use one's sterilized hands without needing to rub in and/or let his/her hands dry which is typically required by use of liquid/gel sanitizers.

Still another advantage of the present UV pathogen control device and system is that the present device and system generates ozone by utilizing oxygen exposed to UV light.

And yet another advantage of the present UV pathogen control device and system is that the present device and system do not leave a user's hands cold, sticky and smelly as is common when using common liquid/gel sanitizers.

Further, another advantage of the present UV pathogen control device and system is that the present device and system reduces landfill waste associated with single use disposable plastic bottles which currently store sanitizing liquids/gels.

Yet another advantage of the present UV pathogen control device and system is that the present device and system does not require the use of any chemicals on the surface to be sterilized.

For a more complete understanding of the above listed features and advantages of the UV pathogen control device and system reference should be made to the detailed description and the drawings. Further, additional features and advantages of the invention are described in, and will be apparent from, the detailed description of the preferred embodiments.

DESCRIPTION OF THE INVENTION

Figure 1A:
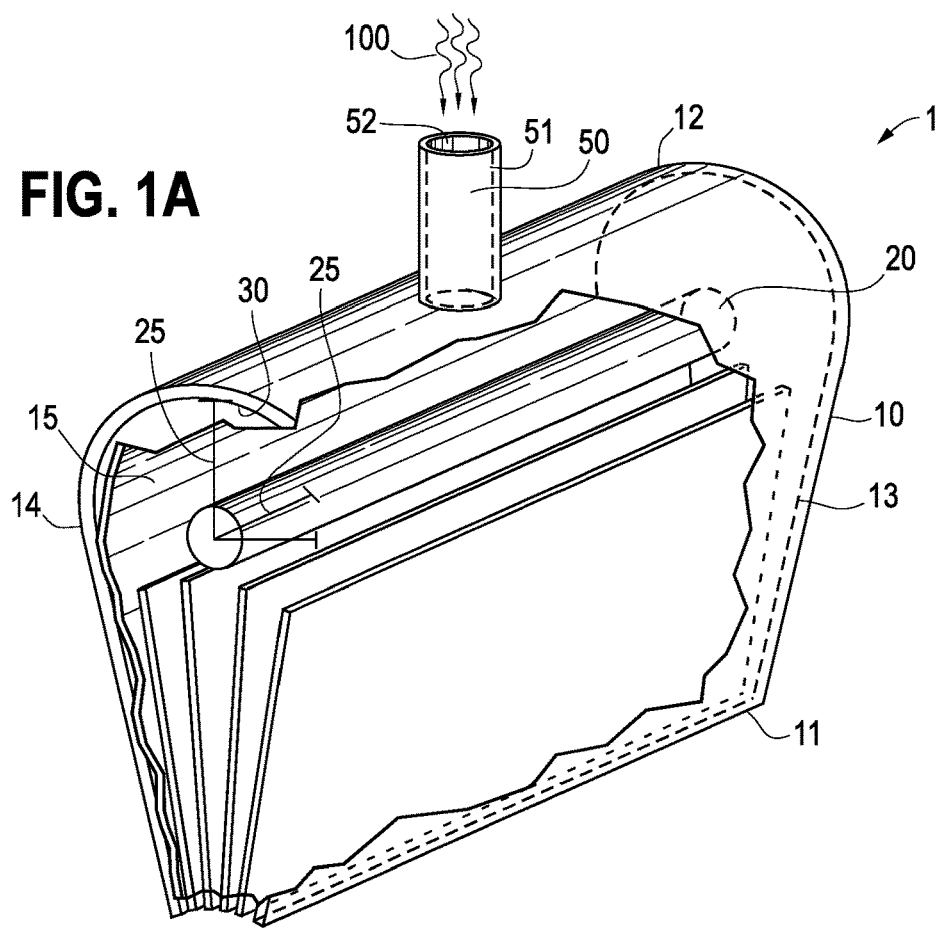
FIG. 1A illustrates a perspective interior view of an example of the UV pathogen control device of the present invention.

Throughout the present specification and the accompanying claims the words "comprise" and "include" and variations thereof, such as "comprises," "comprising," "includes," and "including" are to be interpreted inclusively. That is, these words are intended to convey the possible inclusion of other elements or integers not specifically recited, where the context allows. No language in the specification should be construed as indicating any non-claimed element essential to the practice of the invention.

The terms "a" and "an" and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximate") one particular value, and/or to "about" (or "approximate") another particular value. When such a range is expressed, another embodiment includes from the one particular value and/or to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that is "less than or equal to the value" or "greater than or equal to the value" possible ranges between these values are also disclosed, as appropriately understood by the skilled artisan. For example, if the value "10" is disclosed, the "less than or equal to 10" as well as "greater than or equal to 10" is also disclosed.

All methods described herein can be performed in any suitable order unless otherwise indicated herein or otherwise clearly contradicted by context. The use of any and all examples, or exemplary language (e.g., "such as" or "e.g.," or "for example") provided herein is intended merely to better illuminate the invention and does not pose a limitation on the scope of the invention otherwise claimed.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

The abbreviations used herein have their conventional meaning within the mechanical, chemical, and biological arts.

As used herein, the term "about" refers to a range of values of plus or minus 10% of a specified value. For example, the phrase "about 200" includes plus or minus 10% of 200, or from 180 to 220, unless clearly contradicted by context.

As used herein, the terms "amount effective" or "effective amount" mean an amount, which produces a desired effect, such as a biological effect. In particular, an effective amount of a UV dosage is an amount, which inhibits the growth of a microorganism by at least 90% (by at least 1 log reduction), by at least 99% (by at least 2 log reduction), by at least 99.9% (by at least 3 log reduction), by at least 99.99% (by at least 4 log reduction), by at least 99.999% (at least 5 log reduction), or by at least 99.9999% (at least 6 log reduction). In another embodiment, the effective amount is an amount which kills at least 90% of a target group of organisms.

As used herein, the terms "connect to," connected to," "attach to" or "attached to" or grammatical equivalents thereof mean to fasten on, to fasten together, to affix to, to mount to, mount on, to connect to, to join, to position onto, to position into, to place onto, or to place into. "Attachment" means the act of attaching or the condition of being attached. Attachment can be direct or indirectly. For example a part A may be attached directly to part B. Alternatively, part A may be attached indirectly to part B through first attaching part A to part C and then attaching part C to part B. More than one intermediary part can be used to attach part A to part B. Attaching can be permanent, temporarily, or for a prolonged time.

As used herein, the terms "inhibiting the growth of a microorganism," "inhibiting the growth of a population of microorganisms," "inhibiting the growth of one or more species of microorganisms" or grammatical equivalents thereof refer to inhibiting the replication of one or more microorganisms and may include destruction of the microorganism(s). Assays for determining inhibiting the growth of a microorganism are known in the art.

As used herein, the terms "inhibiting the growth of a pathogen," "inhibiting the growth of a population of pathogens," "inhibiting the growth of one or more species of pathogens" or grammatical equivalents thereof refer to inhibiting the replication of one or more pathogens and may include destruction of the pathogen(s). Assays for determining inhibiting the growth of a pathogens are known in the art.

As used herein, the terms "microorganism" or "microbe" comprise a diverse group of microscopic organisms, including, but not limited to, bacteria, fungi, viruses, archaea, and protists. As used herein, microorganism includes pathogens.

The terms "optional" or "optionally" as used throughout the specification means that the subsequently described event or circumstance may but need not occur, and that the description includes instances where the event or circumstance occurs and instances in which it does not. The terms also refer to a subsequently described composition that may but need not be present, and that the description includes instances where the composition is present and instances in which the composition is not present.

As used herein, the term "portable" in the context of a UV device refers to a UV device of the present invention that can be carried by a person and that can be temporarily (e.g., for the duration of a sanitization cycle) attached to a container, a room, a space, or a defined environment.

As used herein, the term "radiation" or grammatical equivalents refer to energy, which may be selectively applied, including electron beam radiation, gamma radiation, x-ray radiation, light such as ultraviolet (UV) light, visible light, and infrared light, microwave radiation, and radio waves. A preferred radiation is UV light radiation. "Irradiation" refers to the application of radiation to a surface.

As used herein, the terms "sterile" or "sterilization" and grammatical equivalents thereof refer to an environment or an object, which is free or which is made free of detectable living cells, viable spores, viruses, and other microorganisms. Sometimes the process of sterilization is also referred herein to as "disinfection" or "sanitization." In embodiments of the present invention, the term "sterilization" includes "effective sterilization," which is effectively inhibiting the growth of a microorganism as defined herein. Inhibiting the growth of a microorganism by at least 90% (by at least 1 log reduction), by at least 99% (by at least 2 log reduction), by at least 99.9% (by at least 3 log reduction), by at least 99.99% (by at least 4 log reduction), by at least 99.999% (at least 5 log reduction), or by at least 99.9999% (at least 6 log reduction), for example.

As used herein the term "ultraviolet" and the abbreviation "UV" refer to electromagnetic radiation with wavelengths shorter than the wavelengths of visible light and longer than those of X-rays. The UV part of the light spectrum is situated beyond the visible spectrum at its violet end. Unless specified to the contrary, UV includes "UV-A," which refers to ultraviolet light in the range of 315-400 nanometers (nm). UV also includes "UV-B," which refers to ultraviolet light in the range of 280-315 nanometers (nm). UV also includes "UV-C," which refers to ultraviolet light in the range of 200-280 nanometers (nm).

As used herein, the terms "ultraviolet radiation" or "UV radiation" refer to radiation having a wave-length or wavelengths between from 160 to 400 nm. If a range is specified, a narrower range of radiation is meant within the 160 to 400 nm range. The range specified, unless otherwise indicated, means radiation having a wavelength or wavelengths within this specified range.

In the following description it is to understood that terms such as "forward," "rearward," "front," "back," "right," "left," upward," "downward," "horizontal," "vertical," "longitudinal," "lateral," "angular," "first," "second" and the like are words of convenience and are not to be construed as limiting terms.

One aspect of the preset invention is a UV microorganism/pathogen control device and system which utilizes high velocity air flow in conjunction with UV light from multiple reflective surfaces to kill pathogens is provided. The UV pathogen control device and system is especially suitable for organic and inorganic sterilization of surfaces through the combination of introduction of wave lengths in the UV spectrum and the chemical effects caused by UV in the presence of certain gases. The device is suitable for use in, for example, medical facilities, schools, restaurants, airports, cruise ships, senior living centers and the typical office space to prevent the proliferation of pathogens by people and objects. The present device also reduces the buildup of environmental waste from plastic bottles caused by current use of disposable sterilization devices like gels and liquids in plastic bottles.

Referring first to FIG. 1A, in an embodiment, a UV pathogen control device 1 (herein after "UV device") is illustrated. The UV device 1 may have a control head/housing 10 having a front 11, back 12, a first side 13, a second side 14, a top 15, a bottom 16, and a generally hollow interior 17. Preferably, the UV device 1 is made largely of a durable material such as metal or a durable plastic. In an embodiment, the UV device 1 is generally tear-drop shaped, having a smaller front 11 than the back 12 and wherein the back 12 is generally curved. The first side 13 and the second side 14 may be non-parallel, with their lines of axis meeting just in front of the front 11 surface of the UV device 1. In one embodiment, the angle between the first side 13 and the second side 14 of the UV device 1 is approximately between 20 and 50 degrees for optimal results. It should be understood that the angles may vary and still allow the device 1 to operate properly.

In one embodiment, the interior surface is, or is coated with a reflective material. The reflective material may be aluminum. In another embodiment, the interior surface is chosen from aluminum, including polished aluminum, UV-enhanced Aluminum, aluminum oxide aluminum, and UV-enhanced aluminum oxide aluminum.

Located within the generally hollow interior 17 of the UV device 1 may be a UV light source 20. In one embodiment, the UV light source 20 is generally cylindrical in shape, extending predominately from the top 15 of the UV device 1 to the bottom 16 of the UV device 1. In particular, the UV light source 20 may be generally a rod which allows air 100 to circulate around it and wherein the UV light source 20 remains a constant distance 25 from the curved interior surface 30 of the back 12 of the UV device 1.

The exact nature of the UV light source is not known to be critical, as long as it is a germicidal light source. In embodiments of the present invention, the light source can include a low pressure mercury lamp, a medium pressure mercury lamp, a high pressure mercury lamp, an ultra-high pressure mercury lamp, a low pressure short arc xenon lamp, a medium pressure short arc xenon lamp, a high pressure short arc xenon lamp, an ultra-high pressure short arc xenon lamp, a low pressure long arc xenon lamp, a medium pressure long arc xenon lamp, a high pressure long arc xenon lamp, an ultra-high pressure long arc xenon lamp, a low pressure metal halide lamp, a medium pressure metal halide lamp, a high pressure metal halide lamp, an ultra-high pressure metal halide lamp, a tungsten halogen lamp, a quartz halogen lamp, a quartz iodine lamp, a sodium lamp, and an incandescent lamp.

In some embodiments, a UV light source of the present invention comprises a low pressure mercury lamp. In some embodiments, a UV light source of the present invention comprises a medium pressure mercury lamp. In some embodiments, a UV light source of the present invention comprises a high pressure mercury lamp. In some embodiments, a UV light source of the present invention comprises an ultra-high pressure mercury lamp. Such mercury lamps are known in the art and are commercially available, e.g., Steril Aire Model SE series UVC Emitters™.

In some embodiments, a UV light source of the present invention comprises a low pressure short arc xenon lamp. In some embodiments, a UV light source of the present invention comprises a medium pressure short arc xenon lamp. In some embodiments, a UV light source of the present invention comprises a high pressure short arc xenon lamp. In some embodiments, a UV light source of the present invention comprises an ultra-high pressure short arc xenon lamp. Short arc xenon lamps are known in the art and are commercially available, e.g., Ushio #5000371-UXL-75XE Xenon Short Arc Lamp.

In some embodiments, a UV light source of the present invention comprises a low pressure long arc xenon lamp. In some embodiments, a UV light source of the present invention comprises a medium pressure long arc xenon lamp. In some embodiments, a UV light source of the present invention comprises a high pressure long arc xenon lamp. In some embodiments, a UV light source of the present invention comprises an ultra-high pressure long arc xenon lamp. Long arc xenon lamps are known in the art and are commercially available, e.g., Lumi-Max XLA1500 W Long Arc Xenon Lamp.

In some embodiments, a UV light source of the present invention comprises a low pressure metal halide lamp. In some embodiments, a UV light source of the present invention comprises a medium pressure metal halide lamp. In some embodiments, a UV light source of the present invention comprises a high pressure metal halide lamp. In some embodiments, a UV light source of the present invention comprises an ultra-high pressure metal halide lamp. Metal halide lamps are known in the art and are commercially available, e.g., Venture Lighting product number 32519, open rated 175 watt probe start lamp.

In some embodiments, a UV light source of the present invention comprises a halogen lamp. A halogen lamp includes, but is not limited to a tungsten halogen lamp, a quartz halogen lamp and a quartz iodine lamp. Halogen lamps are known in the art and are commercially available, e.g., General Electric model 16751.

In some embodiments, a UV light source of the present invention comprises a sodium lamp. A sodium lamp includes, but is not limited to a high pressure sodium lamp. Sodium lamps are known in the art and are commercially available, e.g., General Electric ED18, 400 W, high pressure sodium lamp.

In some embodiments, a UV light source of the present invention comprises an incandescent lamp. An incandescent lamp includes, but is not limited to an electric light filament lamp. Incandescent lamps are known in the art and are commercially available, e.g., Philips 60-Watt Household Incandescent Light Bulb.

In some embodiments, a UV light source of the present invention comprises a light emitting diode (LED) or a solid state light emitting device, including, but not limited to a semiconductor laser. LEDs are known in the art and are commercially available, e.g., Model L-A3W Energy Efficient UV 110V LED Spot light from Battery Junction.

When more than one light source is used, each one can be independently selected.

In some embodiments, a UV source can be used that does not inherently generate ozone. With this embodiment, an external ozone generator can be used. In some embodiments, a second lamp can be used that produces wavelengths that produce ozone.

Where the UV source is a non-ozone producing such as a krypton chloride lamp/module with a 222 nm output the ozone is produced either by another lamp producing wavelength in the 170 to 190 nm separate from the UV sources used for sterilizing-surface exposure. One example of this configuration is a device using UV sources mounted in flat modules. The modules may be laid out to fit the geometry. If, for example, the UV device is used for hand sterilization there can be modules above and below with a gap of sufficient spacing to allow a hand to enter and pass under the arrangement. Optionally, special geometry lamps, square, planar or smaller tubular sources in the place of the modules. In any of the geometries the spacing may be adjusted such that some wavelengths are attenuated to more acceptable levels as ozone will block/attenuate specific wavelengths. It is also possible to use other inert gases inject into the space to further attenuate unwanted wavelengths.

Without being bound by theory or mechanism, in embodiments of the present invention the ozone is preferably injected under pressure and with sufficient momentum to overcome any hydrostatic boundary layer surrounding the target surface, either directly or through the turbulent flow at the surface to be sterilized. In the case of the modular design where the ozone is not specifically generated by the UV source, the ozone is generated by another lamp that generates wavelengths that are conducive to generate ozone or by coronal generators well known in the art. In this embodiment, either air or recirculated-return from the sterilizing device where the chamber is not open and the air supply device keeps the chamber in negative pressure so the ozone is confined to the chamber inside thus limiting local contamination of the ozone into breathing spaces to less than 0.1 ppm. The recirculation also allows higher levels of ozone to be generated with less energy expenditure.

In one embodiment, predominately the entire interior surfaces 31 of the interior 17, including a plurality of reflective plates 200A-200D, of the UV device 1 is reflective. The interior surfaces 31 are reflective so as to properly direct the UV light 55 from within the interior 17 of the UV device 1 toward the plurality of reflective plates 200A-200D wherein the UV light 55 is further properly reflected and directed out of an opening 75 of the front 11 of the device 1. The specific arrangement of the plurality of reflective plates 200A-200D is designed to have a reduced angular displacement between the reflective plates 200A-200D so as to produce a uniform distribution of the leading edges 275 of the closest to the UV light source 20. As a result, the UV light 55 which ultimately exits out the opening 75 of the front 11 of the device 1 is both concentrated and focused. The plurality of reflective plates 200A-200D provide a high efficiency wave to control and direct the UV light 55 while simultaneously assuring complete $O_2$ to $O_3$ conversion.

In an embodiment, an air input opening 50 is located on, for example, the back 12 of the UV device 1. In an embodiment, the air input opening 50 may be a generally cylindrical tube 51 having a hollow passageway 52 which allows the inflow of air 100 into the interior 17 of the UV device 1. Preferably, the air 100 is pressurized. The air input opening 50 may be connected to a tube (not shown) and an air compressor (not shown) which supplies air 100 to the interior 17 of the UV device 1. Preferably, a filter is located in the compressor so as the air 100 delivered to the interior 17 of the UV device 1 is largely free of dust and other particles.

Figure 2A:
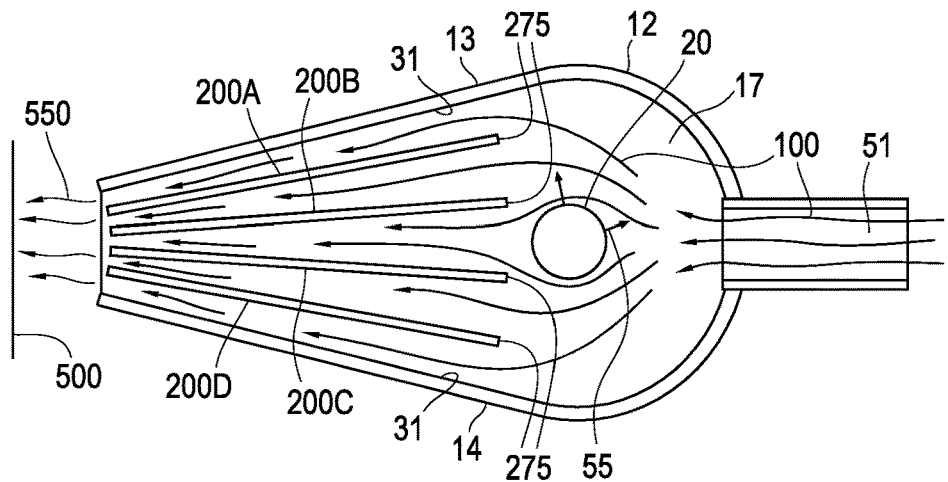
FIG. 2A illustrates a side view of the interior of an example of the UV pathogen control device of the present invention wherein a typical path of the ozone is shown.
Figure 2B:
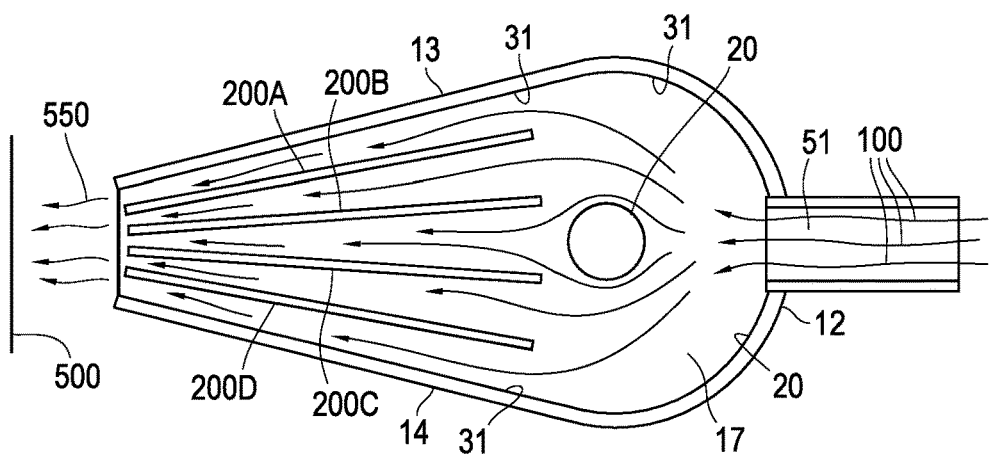
FIG. 2B illustrates a side view of the interior of the UV pathogen control device wherein a typical path of the air is shown.
Figure 2C:
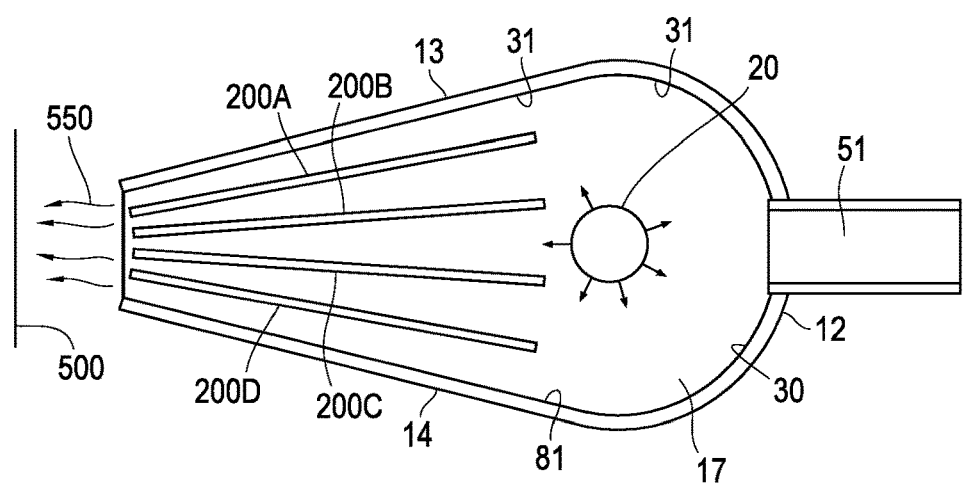
FIG. 2C illustrates a side view of the interior of the UV pathogen control device wherein a typical path of the UV light is shown.

Referring now to FIGS. 2A-2C, in an embodiment, a plurality of reflective plates 200A, 200B, 200C and 200D may be located within the interior 17 of the UV device 1. Although the figures illustrate the UV device 1 having four reflective plates 200A-D, it is understood that the UV device 1 may have a greater or fewer number of reflective plates 200A-D. In an embodiment, the two exterior or ('outside') reflective plates 200A and 200D (in FIG. 2A) may be parallel to the exterior sides 13, 14 of the UV device 1. As a result, UV light 55 which passes between the exterior reflective plates 200A and 200D and the exterior sides 13, 14 of the UV device 1 and finally out of the elongated opening 75 at the front 11 of the UV device 1 will hit the desired surface 500 to be sterilizes at approximately 0 to 40 focused and concentrated angle. In an embodiment, the surface 500 to be sterilized may be, for example, a person's hand, a computer, a work area or any other surface. In an embodiment, the plurality of reflective plates 200A-200D not only direct the UV light 55 toward the elongated opening 75 of the UV device 1, but the plurality of reflective plates 200A-200D also direct the compressed air 100 toward the opening 75 where the compressed air 100 and UV light 55 is then combined. Thus, the reflective plates 200A-200B are multifunctional.

In an embodiment, the reflective plates 200A-D may be, for example, fused quartz plates. The reflective plates 200A-D may be made from, for example, quartz. The use of the quartz for the plurality of reflective plates 200A-200D may have at least two benefits. Although most of the UV light is reflected because the shallow angles, some of the incident UV will be at such an angle (some of the UV internal bounce is highly randomized) that some might be refracted through the plurality of reflective plates 200A-200D so the material reflects, refracts and absorbs—and would be pass through to the next reflective layer with low loss. Whereas a hard-reflector can either reflect or absorb the UV. In an embodiment, the compressed air 100 which enters the interior 17 of the UV device 1 may be struck by the UV light 55 generated by the UV light source 20. For illustrative purposes in FIGS. 2A-2C, the compressed air 100 is illustrates in dotted lines whereas the UV light 55 is illustrated as solid lines. Quartz is only one example of viable reflective materials. Although missing the refractive aspects hard reflective surfaces can be effectively used with a small loss of output efficiency.

In one embodiment, the reflective plates are, are coated with, aluminum. In another embodiment, the reflective plates are chosen from aluminum, including polished aluminum, UV-enhanced aluminum, aluminum oxide aluminum, and UV-enhanced aluminum oxide aluminum.

The UV light source 20 expels UV light 55 at approximately a 160 to 400 nanometer wavelength which interacts with the compressed air 100 (specifically, an $O_2$ molecule) and therein generates ozone $(O_3)$ 550 (FIG. 2A) after an initial latency period. More specifically, ozone conversion rates are not instantaneous. The act of the generation of ozone absorbs 187 nm line and reduces neighboring UV spectra lines, for example, ozone layer protecting the earth from UV. The fact that ozone is generated inherently profiles the UV spectral output to be more like sunshine with lesser of the shortest wavelengths. For illustrative purposes, while FIG. 2A illustrates the path of the ozone 550 within the interior 17 of the UV device 1, FIG. 2B illustrates the path of the compressed air 100 without activating the UV light 55 and FIG. 2C illustrates the path of the UV light 55 without the introduction of the compressed air 100.

The ozone 550 created within the interior 17 of the UV device 1 from the interaction of the UV light 55 and the compressed air 100 then reflects off of the plurality of reflective plates 200A-D and exits the elongated opening 75 at the front 11 of the UV device 1. When the ozone 550 then interacts with a pathogen or other harmful substance, the ozone 550 sterilizes the pathogen or other harmful substance and a sterilized environment is created.

Figure 1B:
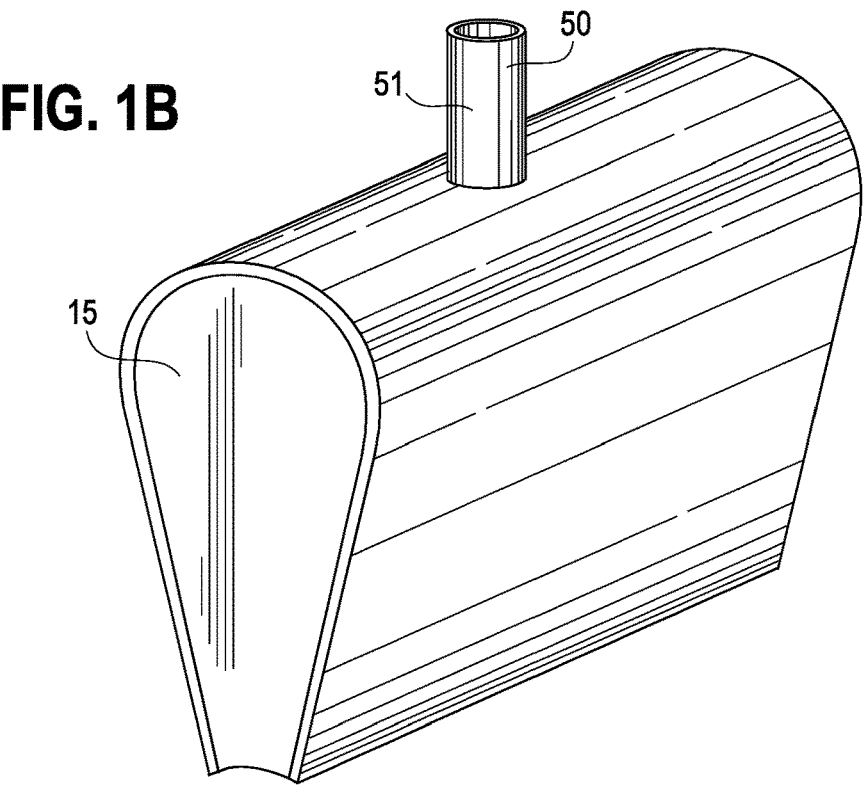
FIG. 1B illustrates a perspective exterior view of an example of the UV pathogen control device of the present invention.
Figure 5:
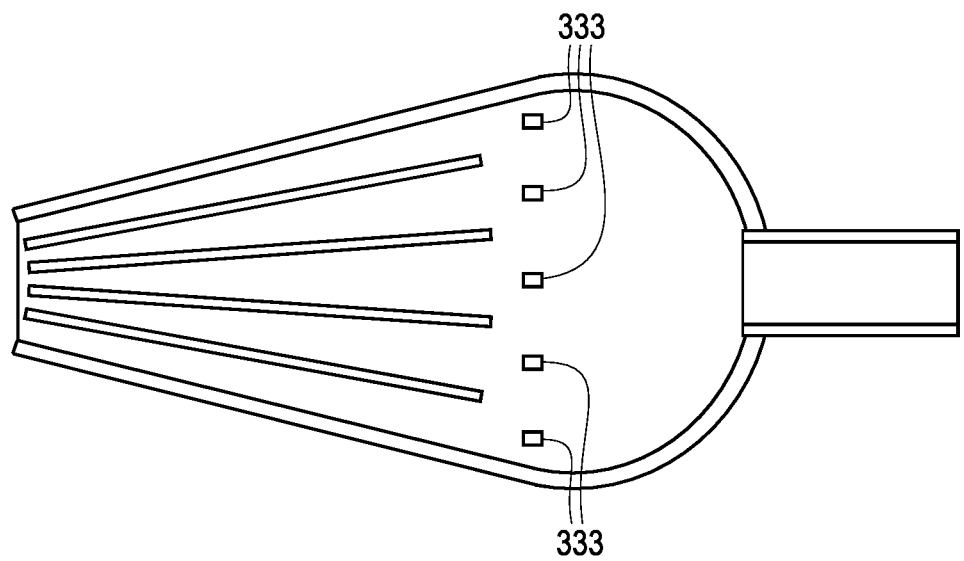
FIG. 5 illustrates an alternative embodiment showing LED UV lights feeding the UV light into the interior of the UV device and the plurality of reflective quartz plates.

FIG. 5 illustrates an alternative embodiment of the design of FIGS. 1-2C. In this alternative embodiment, the UV device 1 may have a plurality of LED UV lights 333 feeding the UV light 55 to the compressed air 100 within the interior 17 of the device 1 instead of the single cylindrical UV light source 20. In this embodiment, the LED UV lights 333 may be a plurality of different lights wherein each LED UV light 333 is located between either two of the plurality of reflective plates 200A-200D or between an outside reflective plate 200A or 200D and the interior wall 31 of the UV device 1. In one embodiment, because this version with the plurality of LED UV lights 333 has multiple light sources 333, a user may program the LED UV lights 333 to different wavelengths. This may result in a more efficient device 1 in that the ozone 550 which exits the elongated opening 75 at the front 11 of the device 1 may be more powerful and efficient. Ozone generation by well know coronal discharge may be substituted where a UV diode is not available in the correct wavelength range for the generation $O_3$ by UV absorption. This could be done in the chamber area 17 around the UV source or separately in the air flow path 100 to the UV device.

Figure 3:
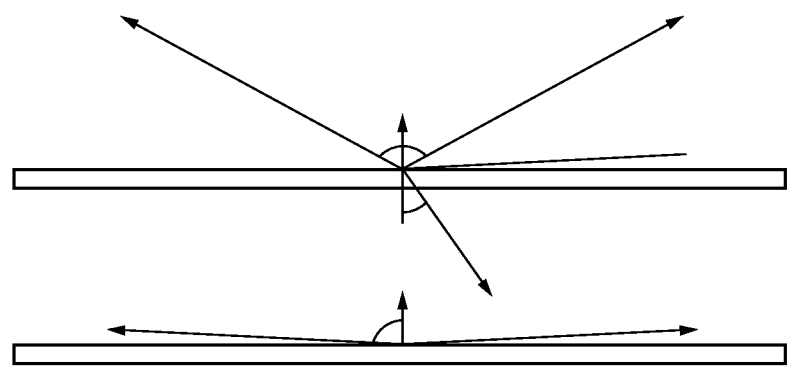
FIG. 3 illustrates Snell's law and reflection versus refraction showing that shallow angle incidence results in very low refractive component of the reflective quartz plates.

Again, without being bound by theory or mechanism, UV's short wavelength makes it prone to absorption at an atomic level. Even a good reflector in the optical range may be ineffective for UV. For example, silver is only 80% reflective and some aluminum reflectors are only 85%. In a low cost embodiment, the plurality of reflective plates 200A-200D may be made from an alloy of aluminum. This, however, may result in a lower light output due to the fact that the ozone is created primarily in the interior 17 of the device 1 around the light source 20 before it enters the plurality of reflective surfaces 200A-200D and, potentially, the light output might actually be increased with more reflection. The solution is to introduce the UV light 55 into the interior 17 of the UV device 1 where the angle of incidence is very shallow. This can be seen in FIG. 3 where one of the outside reflective plates 200A is parallel to the interior wall 31 of the UV device 1 and the incident ray is therefore at a moderate angle. The UV light 55 therefore splits into a reflected ray 49 and a refracted ray 50. According to Snell's law the incident ray 48 at angle θ1 and the angle of the reflected ray θ2 49 are identical the refracted ray θ3 49 is angle is reduced by index of refraction Na (54). And the magnitude of the split is variable depending on the angle. If the incident ray 48 were orthogonal to the reflective plate 200A 95% or more would flow into the reflective plate 200A.

Figure 4A:
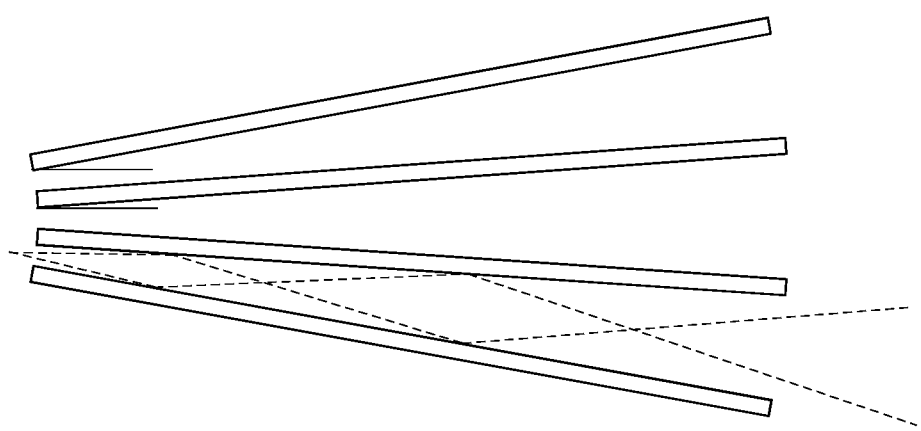
FIG. 4A illustrates the internal reflective quartz plates and the culminating effects to bring the diffuse output of the UV light source where the UV light rays enter the converging inner surface space and are reflected at a shallow angle.
Figure 4B:
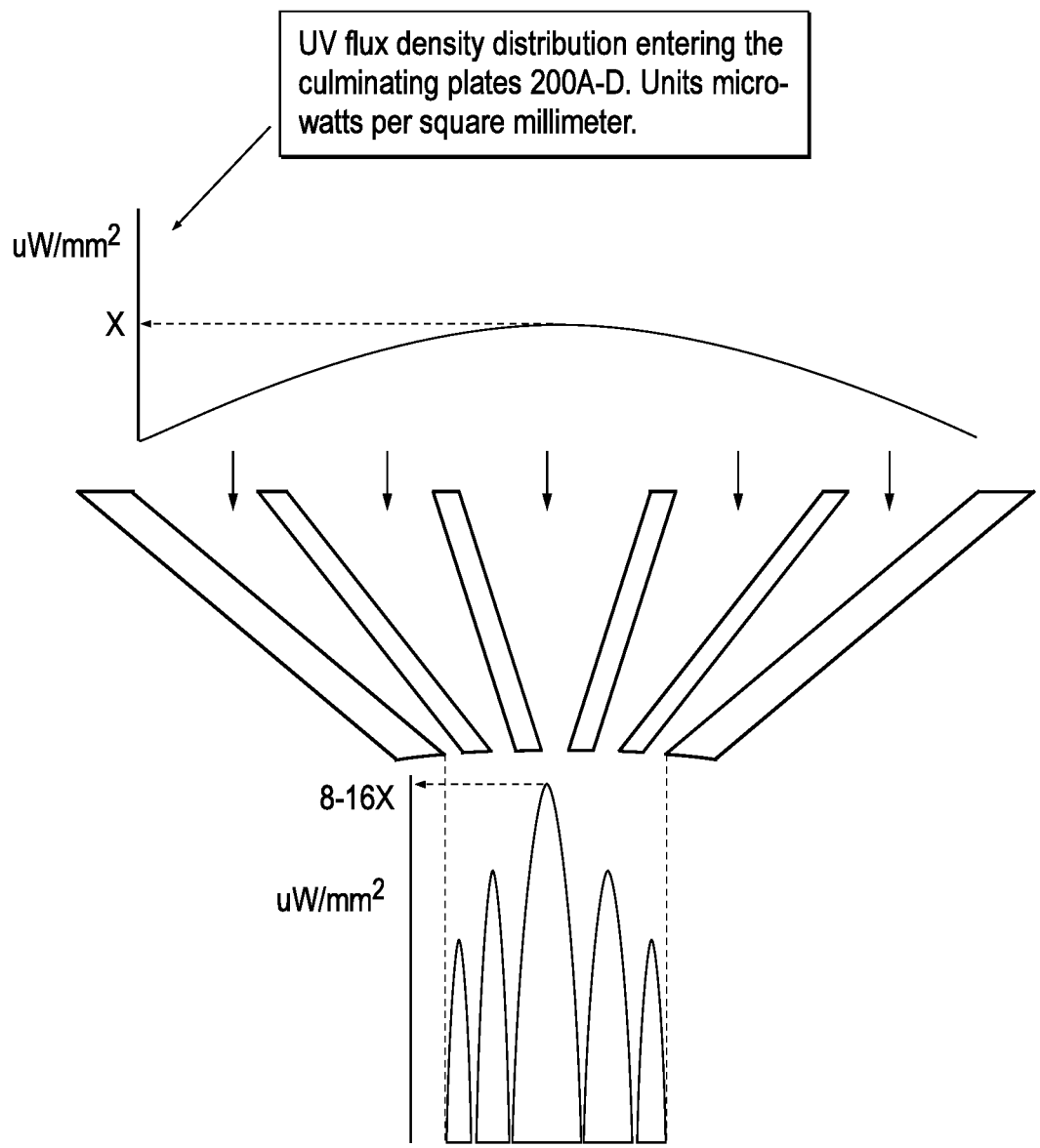
FIG. 4B illustrates a diagram of the culminating effect.

In the case of a shallow angle ray 48 the magnitude of the reflected to the refracted is better than mirrored surface reflection efficiency. The small refraction component is not lost if the plurality of reflective plates 200A-200D are made from quartz. This small component may be ultimately conducted in the quartz longitudinal direction to exit from the elongated opening 75 of the UV device 1. The culminating effect can be seen in FIGS. 4A-4B with symmetrical distribution around the center line.

The number and thickness of the plurality of reflective plates 200A-200D are important in the design. The greater number of plurality of reflective plates 200A-200D the more shallow the angle the higher the reflective efficiency of the device 1. The thicker the plurality of reflective plates 200A-200D the more of the UV light 55 will react with the leading ends 275 of the plates 200A-200D (FIG. 2A) and the less efficient the device becomes. The convergence-angles of the plurality of reflective plates 200A-200D lead to an every narrowing angle where at the elongated opening 75. For design purposes and with quartz construction the maximum should be less than 10 degrees, θ1. As seen in FIG. 4, the angle is progressively smaller on the inner plurality of reflective plates 200B-200C so as to provide for a 'collection space' near the surface 500 to collect a majority of the ozone 550 expelled from the elongated opening 75 of the device 1.

Embodiments of the invention include a control panel. The control panel can have a variety of functions, including velocity of air flow into the interior of the chamber, operation of the UV source, operation of any optional separate ozone production devices, optical sensors, etc. The design and operation of such a control panel is well within the ordinary skill in the art.

Figure 8:
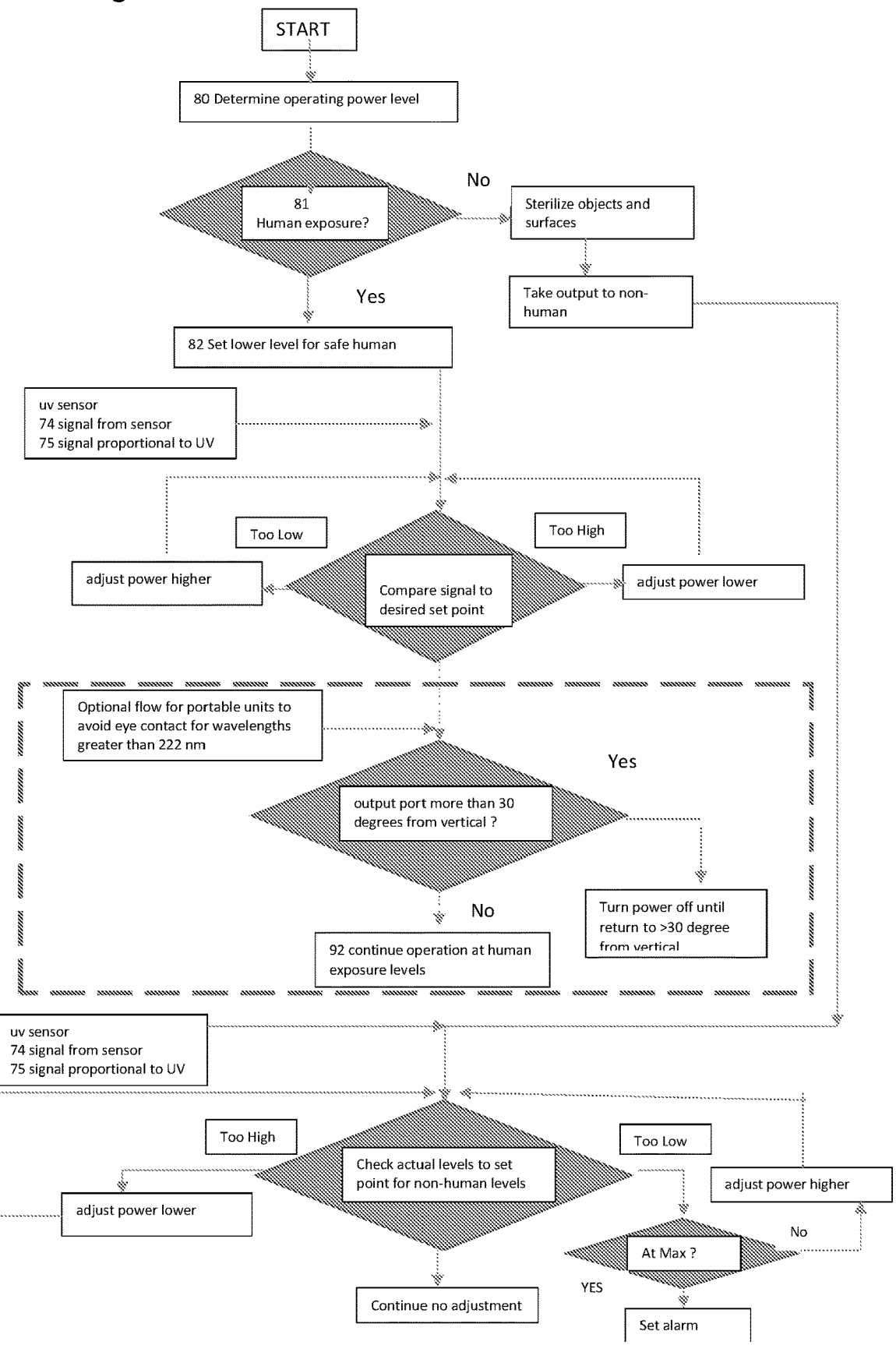
FIG. 8 is a diagram for an exemplary control loop for use with aspects of the present invention.

FIG. 8 is an example of a control loop that can be used for safety of both human and non-human exposure. A control system can set a predetermined power level that is tested for human sterilization or non-living surfaces. In an embodiment, the power levels may be regulated to different levels based on multiple criteria that can be set based on safe exposure levels or levels that are tailored for either surface types of pathogenic nature. For example, power levels are regulated to different levels based on multiple criteria that can be set based on safe exposure levels or levels that are tailored for either surface types of pathogenic nature. The most fundamental may starts at Block 80 where the unit is powered on and then determines the level of operation. Block (81) is then selected automatically to deliver the correct power level for either human exposure (skin surfaces) or non-living (tools, cloth, etc.) where higher power can be applied. The selection block (81) can be manual such as a switch or through the use of an automatic profile selection. Block (82) establishes the output power and then enters a control loop of block (86) where input from sensors (74, 75) in block (85) is compared to the correct level and adjusted to compensate for aging UV source or loss of transmission or reflectance as a result of dirt on the internal surfaces, for example.

Optionally other control schemes can be implemented such as but not limited to having the device output port is always at an angle such that eye exposure is not possible. This is seen in block (89) where a sensor could detect the angle of the present invention would shut the output off if the output port strays from some preset angle Block (90). Once back to normal angle the operation would return.

It is within the level of skill in the art to use the control panel to define the convergence of three parameters UV intensity (mJ/cm2), ozone intensity (ppm at STP) and a mechanical parameter of air velocity where the parameter of measure is m/sec (meters per second) to achieve the desired effects of treating a surface with the present invention.

For example, air velocity can be determined to effectively break down the hydro static layer next to the skin. This effect is described by Poiseeuille's law, and others, where the flow of a fluid next to a surface reduces to near zero at the fluid surface boundary of a flow of any gas or fluid. The human perceptual limit can be defined for air when a puff of air is felt to cool the skin. This occurs at about 0.5 m/sec and is mitigated by human perceptual variability and environmental conditions such as altitude and temperature. Thus, in this example, defining the lower boundary of the velocity of the machine as needing to be above 0.5 m/sec. In an absolute sense there is no upper limit outside of it not being such an intensity as to mechanically damage the skin or surface.

Additionally, UV exposure can be defined in the context of the integral of time and intensity (mj/cm2). Limits are further described by wavelength as various wavelengths have different penetration levels especially when mammalian skin is considered. Two examples of expected modes of operation use the 254 nm wavelengths and 220 nm.

Figure 6:
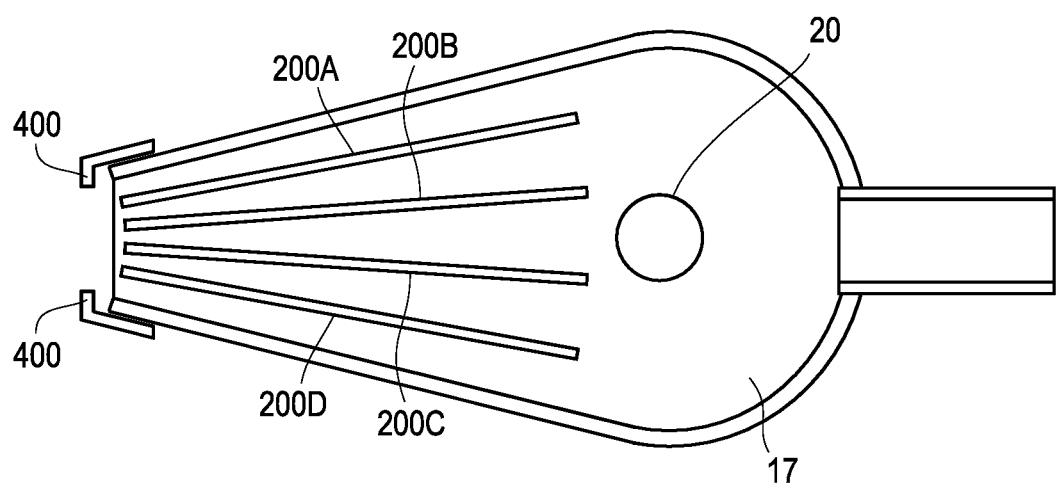
FIG. 6 illustrates an alternative embodiment wherein a sensor is used to measure the UV level and ozone level created by the device.

As illustrated in FIG. 6, in one embodiment, the UV device 1 may have optional sensors 400. The optional sensors 400 may be used to measure and report, for example, the UV light levels, the ozone levels and air pressure created by the UV device 1 so that a user may adjust the settings if necessary. For example, if the UV device 1 is to be used on the skin of a person, the settings may be turned down slightly, whereas if the device 1 is to be used to sterilize a work surface or object the intensity of the device 1 may be increased. Although FIG. 6 illustrates the sensors 400 located outside of the interior 17 of the UV device 1 and also show the sensors 400 used in connection with the main UV light source 20 (as opposed to the plurality of LED UV lights 333) it should be noted that the sensors 400 may be used in those other embodiments as well.

In an embodiment, the sensors 400 may also detect multispectral imaging of a device to automatically monitor and report the total return intensity of an object by recording the absorption and re-emission of UV wavelengths.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

This example demonstrates an embodiment of the present invention. Effectiveness of the present invention was tested at the Vanderbilt University for Infection, Immunology and Inflammation.

Purity plates containing isolates of six different bacteria commonly implicated in nosocomial and community-acquired infections were obtained and resuspended in tryptic soy broth to a 0.5 McFarland standard turbidity. A sterile cotton tip swab was used to streak a uniform lawn of each bacterial isolate onto six Mueller Hinton agar plates. Plates were incubated at 25° C. for 30 minutes before performing the following experiments.

For each microbial pathogen, one plate was subjected to each of the following six conditions: 1) no treatment (positive control plate; plate was not passed thru either HyluxO3 device); 2) exposure to Kr bulb device for 5 sec; 3) exposure to Kr bulb device for 10 sec; 4) exposure to Hg bulb device for 5 sec; 5) exposure to Hg bulb device for 10 sec; 6) exposure to Hg bulb device for 10 sec at ½ power. Plates that were exposed to either HyluxO3 device (Tx label=experimental treatment) were exposed with the edge of the plate with writing moving under the UV and O3 beam first (leading edge), in contrast to the edge of the plate that lacks writing (the lagging edge). All plates were then incubated at 37° C. under standard atmospheric conditions for 24 hours and examined thereafter (Oct. 11, 2019).

A general summary of results is provided for the six microbial pathogens tested because each organism produced similar results, with one notable exception (discussed below).

All positive control plates (top left) produced appropriate growth of a confluent lawn of bacteria covering the entire agar plate surface. Plates passed thru the Kr bulb device for 5 sec showed a robust reduction in colony forming units (CFU's) in the leading edge of the plate compared to control plates. The treatment effect with *Serratia marscesens* and *Klebsiella pneumoniae* is subtle, but the effect is much more pronounced with the other four organisms (*E coli*, MRSA, MSSA, *Pseudomonas aeruginosa* ("Psy a")). Plates passed thru the Kr bulb device for 10 sec showed an even further reduction in CFU's compared to control plates (and plates passed thru the Kr bulb device for only 5 sec); CFU's are on the order of $10^2$ (double digit numbers of CFU's).

Plates passed thru the Hg bulb device (5 sec, 10 sec, and 10 sec at ½ power) showed a dramatic reduction in CFU's compared to control plates and plates passed thru the Kr bulb device; CFU's are on the order of $10^1$ (single digit numbers of CFU's). With the exception of *Serratia* and Kleb pneumo, there was no significant difference in the treatment effects between plates passed thru the Hg bulb device for 5 sec vs. 10 sec vs. 10 sec at ½ power. For the above two organisms, there was a significant difference in the number of CFU's for the plates passed thru the Hg bulb device for 5 sec vs. 10 sec (with either full or ½ power).

In all cases, the leading edge of the plate showed a more pronounced reduction in the number of CFU's compared to the leading edge of the plate.

The device of the present invention decreased the number of pathogenic bacteria on agar plates by multiple orders of magnitude compared to controls that do not pass thru these devices. The Hg bulb device consistently produces a more pronounced reduction in microbial pathogens compared to the Kr bulb device. 10 sec under the Kr bulb device produces a more pronounced treatment effect compared to 5 sec. In most cases, there is no difference in treatment effect regardless of the timing (5 sec vs. 10 sec) and power (full vs. ½) under the Hg bulb device.

This example demonstrated the present invention with respect to *B. atrophaeus* spores, tested at the Vanderbilt University for Infection, Immunology and Inflammation.

*B. atrophaeus* spores were ordered from Crosstex through Thomas Scientific. The reported suspension titer was 2.0e7/ml. Spores were germinated using lysogeny broth agar (LBA) and sheep blood agar (SBA) plates to determine a baseline recovery titer after germination. Titer was calculated by serial dilution on 96 well plates after spores germinated in an incubator at 37° C. and 5% CO2.

100 ul spores in 20% ethanol suspension were inoculated onto sterile glass slides ×3 and allowed to dry overnight. ASM recovered spores from the glass slides with 2000 ul of phosphate buffer solution (PBS) using rubber policeman to determine a baseline recovery titer after inoculation.

100 ul of spores in 20% ethanol suspension were inoculated onto sterile slides ×6 and allowed to dry over 4 hours. 3 glass slides were positive control slides (i.e., were not treated); 3 slides were treatment (tx) slides. Tx slides were passed individually through the device with a Kr bulb for 10 seconds (5 sec in, 5 sec out) facing up; slides were treated with UV light at 222 nm and at 0.3 ppm. ASM recovered spores from the glass slides with 2000 ul of phosphate buffer solution (PBS) using rubber policeman; ASM was blinded to control vs. Tx slides during spore recovery. ASM titered spores on LBA×2 plates per slide and ×3 replicas per plate. Titers were calculated after plate incubation.

It was found that *B. atrophaeus* spores from supplier germinated to an average titer of 3.2e6 cfu/ml. Colonies were more discrete and countable from LBA rather than SBA plates. LBA plates were used for all subsequent titers.

Figure 7A:
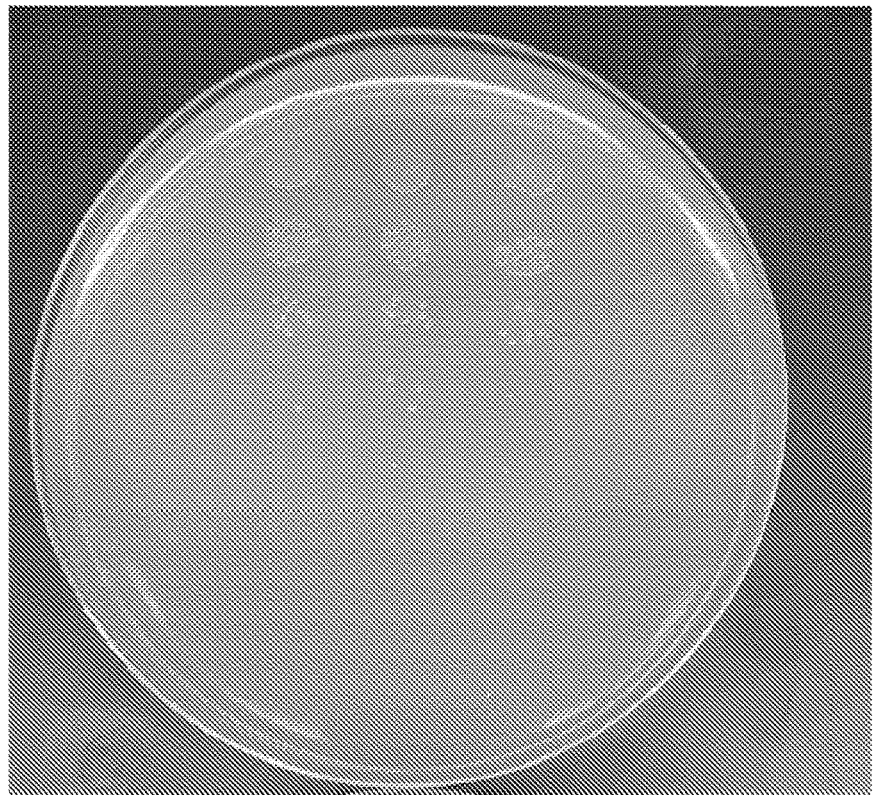
FIGS. 7A and 7B show results from an example of the present invention.
Figure 7B:
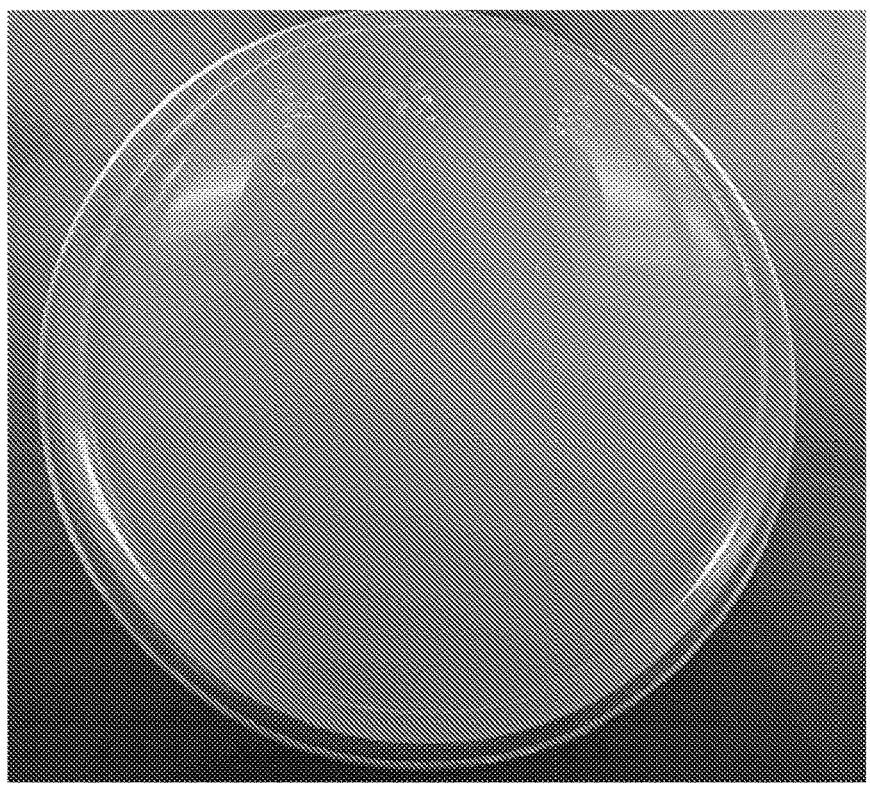

*B. atrophaeus* spores recovered from glass slides germinated to an average baseline titer of 4.0e4 cfu/ml. *B. atrophaeus* spores recovered from control slides germinated to an average of 5.56e4 cfu/ml (range 4.40-6.14 cfu/ml). *B. atrophaeus* spores recovered from tx slides germinated to an average of 164 cfu/ml (range 80-300 cfu/ml). The ratio of control to glass slide spore germination was 339.1. See FIGS. 7A and 7B for a comparison of spore germination.

A device of the invention showed a 339× reduction in *B. atrophaeus* spore germination compared to controls, producing a significant (2 log) reducing in *B. atrophaeus* and confirming clinical utility in reducing transmission of spore-forming pathogens.

All publications mentioned herein are incorporated herein by reference to disclose and describe the methods and/or materials in connection with which the publications are cited.

The invention thus being described, it will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only.

We claim:

1. A UV microorganism inhibiting device, comprising:
a housing having an interior, and a front and back that defines a length;
at least one UV light source located within the interior of the housing;
a pressurized air source to produce pressurized air;
an inlet for introducing pressurized air into the interior of the housing;
reflective surfaces within the interior of the housing; wherein the reflective surfaces are arranged non-parallel to one another along a length of the housing, with the ends of the reflective surfaces toward the bottom side of the housing closer together than the ends of the reflective surfaces toward the top of the housing; and
an outlet opening for allowing UV light and an air/ozone mixture to pass from the interior of the housing to outside the housing.

2. The UV device of claim 1, wherein the housing has first and second sides, a top and bottom; wherein the first and second sides are non-parallel, with their lines of axis meeting in front of the device; and wherein housing is generally shaped for generating an optical convergence.

3. The UV device of claim 2, wherein the housing is generally tear-drop shaped, with the back being generally curved.

4. The UV device of claim 2, wherein the first side and the second side form an angle that is between about 20 and about 50 degrees.

5. The UV device of claim 1, wherein the UV light source is cylindrical or rectangular, and is aligned from the top to the bottom of the device.

6. The UV device of claim 5, wherein the UV light source is selected from the group consisting of a mercury lamp, xenon lamp, krypton lamp, metal halide lamp, tungsten halogen lamp, quartz halogen lamp, a quartz iodine lamp, a sodium lamp, an incandescent lamp, and combinations thereof.

7. The UV device of claim 1, further comprising an air compressor and a control panel to direct pressurized air flow into the device interior and to control operation of the light source.

8. A UV microorganism inhibiting device, comprising:
a control panel;
a housing defining an interior space and having reflective interior surface, and having a top, bottom, and a first side and second side that defines the housing's length;
at least one UV light source located within the interior of the housing;
a pressurized air source;
an inlet for introducing pressurized air into the interior of the housing;
a plurality of planar reflective plates arranged along the length of the interior to provide reflective vectoring for convergence of optical energies of the UV light source at the front of the device; and
an outlet opening for allowing UV light and an air/ozone mixture to pass from the interior of the housing to outside the housing.

9. The UV device of claim 8, wherein the first and second sides are non-parallel, with their lines of axis meeting in front of the front of the device.

10. The UV device of claim 8, wherein housing is generally shaped for generating an optical convergence, at the front of the device, having a smaller front than back.

11. The UV device of claim 10, wherein the housing is tear-drop shaped, having a smaller front than the back, with the back being generally curved.

12. The UV device of claim 8, wherein the plurality of planar plates are non-parallel, with the ends closest to the bottom are closer together at the bottom than at the top.

13. A handheld sanitizing apparatus, as for pathogen reduction on a surface, comprising:
a housing defining an interior space, with an outlet opening communicating with the interior, and a portion of the housing adapted to be gripped by a user;
a ultraviolet (uv) light source mounted within the housing interior, the UV source being chosen to provide one or more wavelengths of light suitable for killing selected pathogens, the UV source mounted in a manner for light to exit through the outlet;
a source of gaseous medium which communicates with the housing interior and exits through the outlet in a stream to contact a surface to be treated by the apparatus;
the housing interior having one or more reflective surfaces with first ends and a second ends arranged to reflect UV light toward the outlet, the reflective surfaces being arranged non-parallel with one another along a length of the housing, with the first ends being toward the outlet of the housing and being closer together than the second ends;
at least part of the gaseous medium including oxygen, the UV light generating ozone within the apparatus interior which is expelled with the stream, the amount of ozone generated and expelled being sufficient to kill selected pathogens exposed to the stream.

* * * * *